(12) United States Patent
Kvaløy et al.

(10) Patent No.: US 6,728,385 B2
(45) Date of Patent: Apr. 27, 2004

(54) VOICE DETECTION AND DISCRIMINATION APPARATUS AND METHOD

(75) Inventors: Olav Kvaløy, Hundhamaren (NO); Georg E. Ottesen, Trondheim (NO); Viggo Henriksen, Trondheim (NO); Sverre Stensby, Trondheim (NO); Svein Sørsdal, Trondheim (NO); Odd Kr. Ø. Pettersen, Trondheim (NO); Jarle Svean, Trondheim (NO)

(73) Assignee: Nacre AS, Trondheim (NO)

( * ) Notice: Subject to any disclaimer, the term of this patent is extended or adjusted under 35 U.S.C. 154(b) by 13 days.

(21) Appl. No.: 10/085,097

(22) Filed: Mar. 1, 2002

(65) Prior Publication Data

US 2003/0165246 A1 Sep. 4, 2003

(51) Int. Cl.[7] .............................................. H04R 25/00
(52) U.S. Cl. ...................... 381/328; 381/71.1; 381/71.5; 381/317
(58) Field of Search ............................. 381/23.1, 71.6, 381/72, 73.1, 312, 314, 315, 317, 318, 320, 321, 322, 330, 331; 704/233; 600/25, 559, 23, 24

(56) References Cited

U.S. PATENT DOCUMENTS

| | | | | | |
|---|---|---|---|---|---|
| 5,201,006 | A | * | 4/1993 | Weinrich | 381/318 |
| 5,509,102 | A | | 4/1996 | Sasaki | 704/219 |
| 5,721,783 | A | * | 2/1998 | Anderson | 381/328 |
| 6,023,674 | A | | 2/2000 | Mekuria | 704/233 |
| 6,415,034 | B1 | * | 7/2002 | Hietanen | 381/71.6 |
| 2002/0141602 | A1 | * | 10/2002 | Nemirovski | 381/328 |
| 2002/0143242 | A1 | * | 10/2002 | Nemirovski | 600/300 |

* cited by examiner

*Primary Examiner*—Curtis Kuntz
*Assistant Examiner*—Brian Ensey
(74) *Attorney, Agent, or Firm*—Young & Thompson

(57) ABSTRACT

An apparatus and a method of voice detection and discrimination apparatus for controlling a voice operated system. A protective ear terminal element in the apparatus protects the ear by providing acoustic attenuation. An inner electroacoustic transducer element on an inner side of the ear terminal element detects a first acoustic field and provides a first electronic signal representing the first acoustic field. An outer electroacoustic transducer element on an outer side of the ear terminal element detects a second acoustic field and provides a second electronic signal representing the second acoustic field. An electronics unit is connected with the electroacoustic transducer elements and includes first and second comparison members.

66 Claims, 9 Drawing Sheets

VOICE DETECTION AND DISCRIMINATION APPARATUS AND METHOD

RELATED APPLICATIONS

The present invention is a further development of the ear terminal described in the international patent applications PCT/NO01/00357, PCT/NO01/00358, PCT/NO01/00359, PCT/NO01/00360, and PCT/NO01/361, which correspond to U.S. application Ser. No.: 09/653,870; Ser. No. 09/653,869; Ser. No. 09/653,868; Ser. No. 09/653,867; Ser. No. 09/653,866; all to be published, and whose subject matter is incorporated herein by reference.

FIELD OF THE INVENTION

The present invention relates to a voice detection and discrimination apparatus in a hearing protection arrangement, and more particularly to a VOX (voice operated transmission/exchange) apparatus, for determining whether an acoustic voice signal is present or absent in a hearing protection arrangement.

The present invention also relates to a method of detecting a voice using the voice detection and discrimination apparatus of the invention in a hearing protection arrangement.

1. Field of Application

Voice activated control is extensively used in communication systems like radio transceivers, intercom systems, recording equipment, etc., and in speech based man-machine-interfaces.

This invention is intended for use in noisy environments, e.g. in environments where some source of acoustic noise is predominant, making it difficult to hear or where damage to the hearing could be at risk. In such environments there could for example be heavy operating machinery or loud vehicle traffic nearby. In other environment there may be large crowds of people. For example in sports stadiums, such as football arenas or the like, where a lot of noise is generated by the audience.

In particular, the primary application for the invention is in situations where it is desirable for people to use a hearing protection arrangement, while still requiring some means of communicating, e.g. to speak with other people or to give commands to voice operated equipment.

2. Prior Art

Present day devices intended to pick up speech from a person in a very noisy environment as a basis for voice detection represent a technological challenge and take several forms. Common types include;

A microphone in close proximity to the mouth, carried on a microphone boom. The microphone is made with a characteristic emphasising the near field from the mouth. This type is often called "noise cancelling".

A vibration pickup in contact with the throat, picking up the vibrations of the vocal cord.

A vibration pickup in contact with the wall of the meatus, the outer ear canal, picking up the vibrations of the tissue in the head.

A similar pickup in contact with the cheek-bone.

A microphone picking up the sound in an enclosed space in the inner portion of the meatus.

Detection of voice is based on several techniques:

Measurement of signal strength of a band-pass filtered microphone/vibration pick-up signal, Advanced signal processing on signal picked up by a microphone (A survey of methods are found in Bishnu S. Atal, Lawrence R. Rabiner: "A Pattern Recognition Approach to Voice-Unvoiced-Silence Classification with Applications to Speech Recognition", IEEE Transactions on Acoustics, Speech and Signal Processing, Vol. ASSP-24, No. 3, June 1976, pp 209–212.

Present day devices often fail to work properly in noisy environments. The following types of errors often take place:

The device is not activated by normal voice

Noise falsely activates the device in case of no speech

OBJECTS OF THE INVENTION

It is an object of the present invention to provide a voice detection and discrimination apparatus providing much improved performance in noisy environments.

It is a further object of the invention to provide a VOX (voice operated transmission/exchange) apparatus which is capable of detecting and discriminating a voice in a noisy environment.

It is yet an object of the invention to provide a voice detection and discrimination apparatus with improved voice detection capability and which has a reduced false activation due to acoustic noise.

In particular, it is a further object of the invention to provide a VOX (voice operated transmission/exchange) apparatus suitable for use with electronic communication systems being used in noisy environments.

It is also an object of the present invention to provide a method of detecting a voice for the control of a voice operated system, by employing an ear terminal element intended also for protecting the hearing function by providing acoustic attenuation.

SUMMARY OF THE INVENTION

According to the invention, these objectives are achieved in a voice detection and discrimination apparatus for controlling a voice operated system comprising a protective ear terminal element for protecting the ear by providing acoustic attenuation. An inner electroacoustic transducer element on an inner side of the ear terminal element detects a first acoustic field and provides a first electronic signal representing said first acoustic field. An outer electroacoustic transducer element on an outer side of the ear terminal element detects a second acoustic field and provides a second electronic signal representing said second acoustic field. An electronics unit is connected with said electroacoustic transducer elements. The electronics unit comprises first comparison means for comparison of said first and second electronic signals in order to obtain the difference between said two electronic signals. The electronics unit also comprises second comparison means for comparing said difference with given criteria. Output means connected to said electronics unit provides an output signal depending on said second comparison. The output signal is used as an input signal to the voice operated system.

According to the invention the objectives are also achieved with a corresponding method of detecting a persons own voice and for controlling a voice operated system, employing an ear terminal element for protecting the ear by providing acoustic attenuation. The method comprises the following steps: The acoustic signal strength on the inner side of said ear terminal element is detected using a first electroacoustic transducer element. The acoustic signal strength on the outer side of the ear terminal element is detected using a second electroacoustic transducer element.

A difference value representing the difference in the acoustic signal strength between the inner and outer side of the ear terminal element is obtained. Using the value representing the obtained difference and given criteria, it is decided if a voice is present. An output signal depending on the decision is provided using an output means. The output signal is used as an input to a voice operated system.

Further preferable embodiments of the invention are defined in the independent claims.

DETAILED DESCRIPTION OF THE INVENTION

Figure 1:
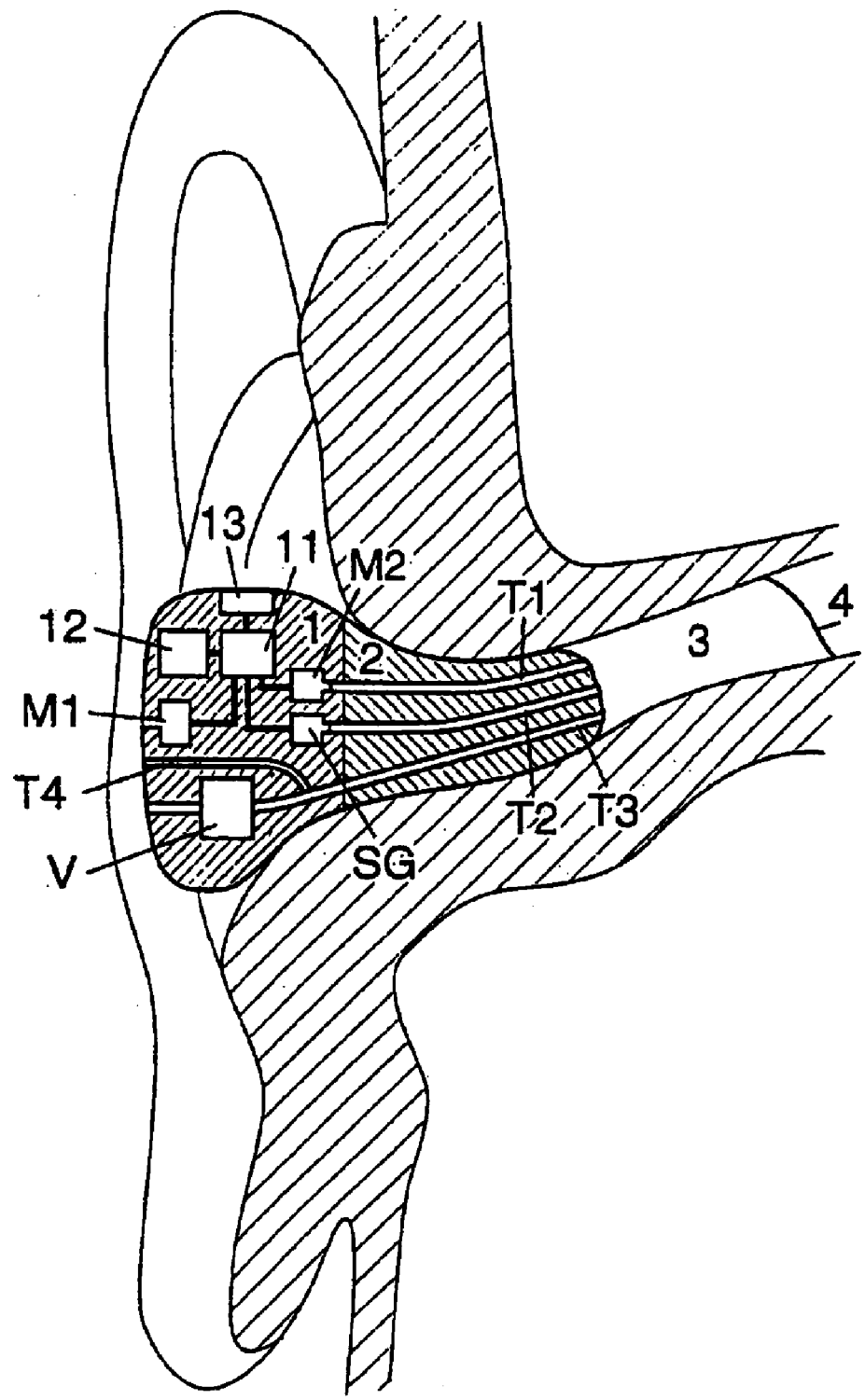
FIG. 1 illustrates an embodiment of the invention where the voice detection is included in an earplug shaped hearing protective voice communication terminal.

FIG. 1 illustrates an embodiment according to the invention where the voice detection and discrimination is included in an earplug based hearing protective voice communication terminal 1,2. The earplug 1,2 comprises a main section 1 containing two electroacoustic transducer elements M1 and M2 and a sound generator SG. The main section 1 is designed in a way that provides comfortable and secure placement in the concha (the bowl-shaped cavity at the entrance of the ear canal). This may be obtained by using individually moulded ear-pieces 1 that are held in position by the outer ear or by providing at least part of the earplug 1,2 with a flexible surrounding pressing against the structure of the outer ear. A sealing section 2 is attached to the main section. The sealing section 2 may be an integral part of the earplug 1,2, or it may be interchangeable. The sound inlet of electroacoustic transducer element M1 is connected to the outside of the earplug 1,2, picking up the external sounds. The electroacoustic transducer element M2 is connected to the inner portion of the meatus 3 by means of an acoustic transmission channel T1. The acoustic transmission channel T1 may contain optional additional acoustic filtering elements. The filtering elements may for instance consist of acoustic resistive elements in the form of porous or sintered inserts, and/or acoustic compliances in the form of small cavities, singly or in combination. An outlet of the sound generator SG is open into the inner portion of the meatus 3 by means of an acoustic transmission channel T2 between the sound generator SG and the inward facing portion of the sealing section 2. The acoustic transmission channel T2 may also contain optional additional acoustic filtering elements.

When smaller electroacoustic transducer elements M2, and sound generators SG are available, it will be possible to mount the electroacoustic transducer element M2 and the sound generator SG at the innermost part of the sealing section 2. Then there is no need for the transmission channels T1 and T2.

The two electroacoustic transducer elements M1, M2 and the sound generator SG are connected to an electronics unit 11, which may be connected to other equipment by a connection interface 13 that may transmit digital or analogue signals, or both, and optionally power.

Electronics 11 and a power supply 12, e.g. a battery, may be included in main section 1 or in a separate section.

One or both of the electroacoustic transducer elements M1, M2 may in a preferred embodiment be microphones, such as standard miniature electret microphones like the ones used in hearing aids. Recently developed silicon microphones may also be used.

The sound generator SG may in a preferred embodiment be based on the electromagnetic or electrodynamic principle, like sound generators applied in hearing aids.

The main section of the earplug 1, 2 may be made of standard polymer materials that are used for ordinary hearing aids. The sealing part 2 may be made of a resilient, slowly re-expanding shape retaining polymer foam like PVC, PUR or other materials suitable for earplugs.

For some applications (less extreme noise levels) the earplug may be moulded in one piece 1,2 combining the main section 1 and the sealing section 2. The material for this design may be a typical material used for passive earpugs (Elacin, acryl).

It is also possible to make the earplug 1,2 in one piece comprising the main section 1 and the sealing section 2, all made of a polymer foam mentioned above, but then the channels T1,T2,T3, have to be made of a wall material preventing the channels T1,T2,T3, to collapse when the sealing section 2 is inserted in the meatus 3. The wall material should be non-porous, typically a plastic or rubber material with a stiffness sufficient to keep the channel open and at the same time allow bending of the channel to conform to the geometry of the meatus.

When the apparatus according to the invention is carried by a user in a noisy environment there will normally be a significant difference in the sound, also referred to as acoustic field or acoustic signal strength between the inside and outside of the apparatus, as detected by the two electroacoustic transducer elements M1 and M2. When the user of the hearing protector speaks, the signal from his voice produces a signal in the inner electroacoustic transducer element M2. The difference in signal strength as detected by the two electroacoustic transducer elements M1,M2 then decreases. When such a decrease in signal difference is detected, this is interpreted as a voice signal being present, and an output for controlling a voice operated system 29 is generated by the output means 13.

In many applications of an apparatus according to the invention, the surrounding pressure may vary during its use. Hence, an equalisation of pressure between the two sides of the earplug system is required. This is obtained by using a very thin duct T3,T4 or a valve that equalises static pressure differences, while retaining strong low frequency sound attenuation. A safety valve V to take care of rapid decompression may be incorporated in the pressure equalization system T3,T4. The pressure equalisation means T3,T4, V are strictly not required in a basic embodiment of the apparatus according to the invention, but may be an optional feature included in another embodiment of the invention.

Figure 2:
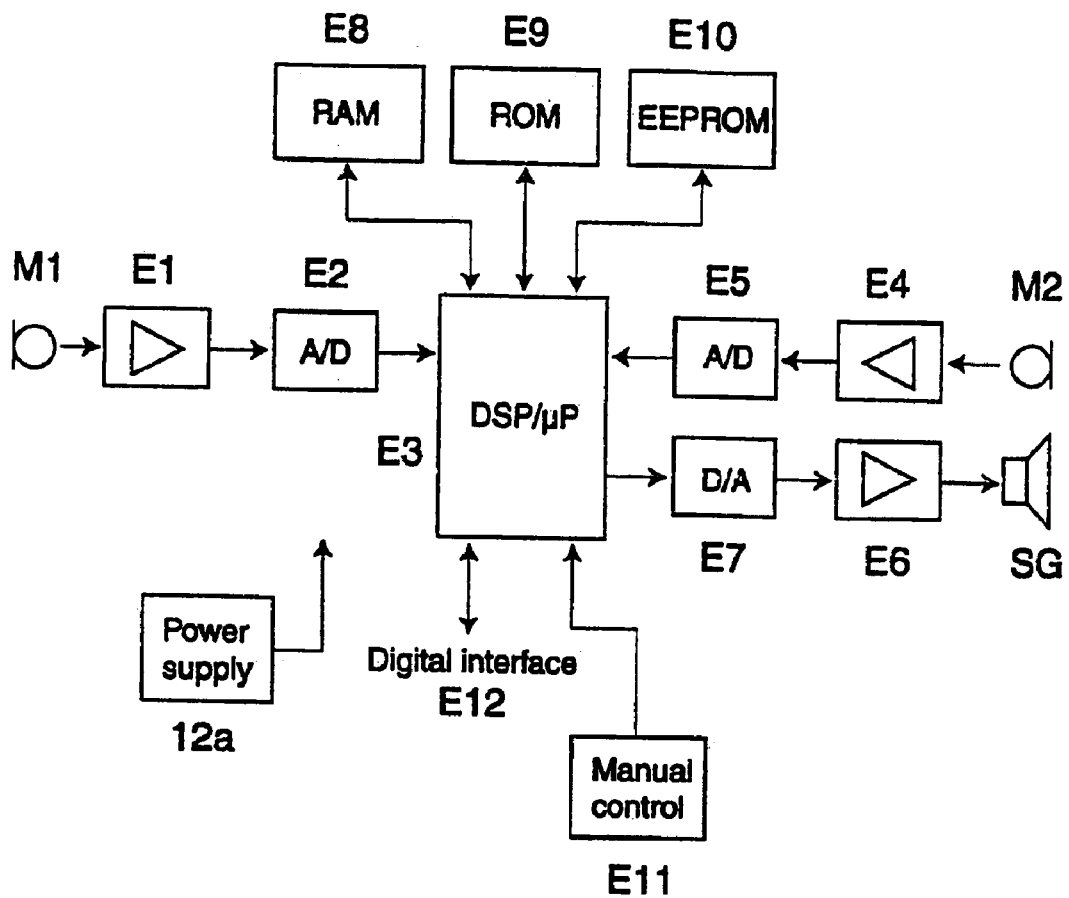
FIG. 2 is a block diagram showing the main functional units of the electronic circuitry of the apparatus according to the invention.

FIG. 2 is a block diagram showing the main functional units of the electronic circuitry of the apparatus according to the invention. The electroacoustic transducer element M1 picks up the ambient sound. A signal from the electroacoustic transducer element M1 is amplified in the amplifier E1 and in a basic embodiment of the invention provided directly for the signal processing unit E3. The signal from the electroacoustic transducer element M1 is in a preferable alternative embodiment of the invention sampled and digitised in an analogue to digital converter E2 and fed to a processing unit E3 that may be a digital signal processor (DSP), a microprocessor (μP) or a combination of both. A signal from electroacoustic transducer element M2, which picks up the sound in the meatus 3 between the isolating section 2 and the tympanum 4, is amplified in the amplifier E4. The amplified signal may either be directly provided for the processing unit E3 or may be sampled and digitised in the analogue to digital converter E5 prior to being fed to the processing unit E3.

For the case that the apparatus according to the invention is being used to control a voice operated system 29 in the form of a communications system, for example using the techniques described in the abovementioned related applications, it will be useful to include a blocking function, as explained below.

An incoming communication signal may be introduced to the processing unit E3 through the digital interface E12. This communication signal is converted to analogue form in the digital-to-analogue converter E7 and fed to the analogue output amplifier E6 that drives the sound generator SG. The sound signal produced by the loudspeaker SG is fed to the tympanum 4 via the canal T2 into the meatus 3.

Figure 5:
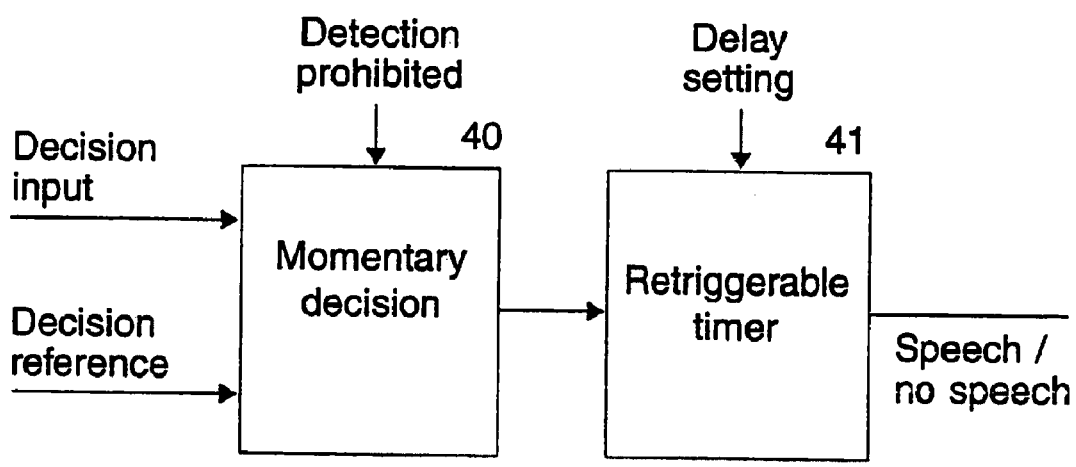
FIG. 5 is a block diagram of the two processing steps of the decision block.

When the incoming communication signal is introduced in the same terminal as is used for voice activated control, it is necessary to apply a blocking function in the form of an additional decision condition signal to the decision process. This additional decision condition signal typically depends on the incoming communication signal. The additional decision condition signal will prohibit or block the detection of the incoming communication signal as if it were the users own voice, during the periods of time when the incoming communication signal is active. This detection prohibition signal is applied to the decision block 28 and the corresponding detail block 40, in FIGS. 3 and 5, respectively.

An incoming communication signal may, however, be introduced into an additional hearing protective terminal (1,2) located in the ear opposite to the ear accommodating the terminal used for voice activated control. In this case the abovementioned blocking function is strictly not required.

The processing unit E3 is connected to storage means which may be RAM (Random access memory) E8, ROM (read only memory) E9, or EEPROM (electrically erasable programmable read only memory) E10, or combinations of these. The memories E8,E9, and E10 are in a preferred embodiment of the invention used for storing computer programs, filter coefficients, analysis data and other relevant data.

The storage means E8,E9,E10 typically contains the criteria to be used by the processing unit E3 during operation of the device. The criteria may typically comprise data provided during assembly of the apparatus, data provided as part of a calibration procedure, possibly associated with particular users, data obtained from adaptive processes during operation of the device or input data, e.g. provided by a user, via the digital interface E12.

The electronic circuitry 11 may be connected to other electrical units by an interface, such as a bi-directional digital interface E12. The communication with other electrical units may be performed via a cable or wireless through a digital radio link. The Bluetooth standard for digital short-range radio is one possible candidate for wireless communication for this digital interface E12. In a preferred embodiment of the invention, signals that may be transmitted through this interface are:

- program code for the processing unit E3
- analysis data from the processing unit E3
- synchronisation data when two ear terminals 1,2 are used in a binaural mode
- digitised audio signals in both directions to and from an ear terminal 1,2.
- control signals for controlling the operation of the ear terminal.
- digital measurement signals for diagnosis of the ear terminal performance.

Based either on the signals received by the electronic circuitry 11 via the communication with other electrical units, on signals stored in the ear terminal element 1,2 itself, or signals detected by the electroacoustic transducer elements M1,M2 the signal processor E3 may generate an output signal for the sound generator SG. In the digital version of the invention the digital signal generated in the processing unit E3 is converted to analogue form in the digital to analogue converter E7 and fed to the analogue output amplifier E6 that drives the loudspeaker SG. The sound signal produced by the loudspeaker SG is fed to the tympanum 4 via the canal T2 into the meatus 3 as described above.

A manual control signal may be generated in the manual control unit E11 and fed to the processing unit E3. The manual control signal may be generated by operating buttons, switches, etc, and may be used to turn the apparatus on and off, to change operation mode, etc. In an alternative embodiment, a voice signal may constitute control signals to the processing unit E3. In this case the detected voice signal would typically be compared with a predetermined, e.g. prerecorded, stored representation of a voice signal, such as a digital recording. A manual control signal may also be provided by a remote unit providing output signals adapted to be received by the apparatus, for example via the interface 13.

The electric circuitry is powered by the power supply 12a that may be a primary or rechargeable battery arranged in the earplug or in a separate unit, or it may be powered via a connection to another equipment, e.g. a communication radio.

Figure 3:
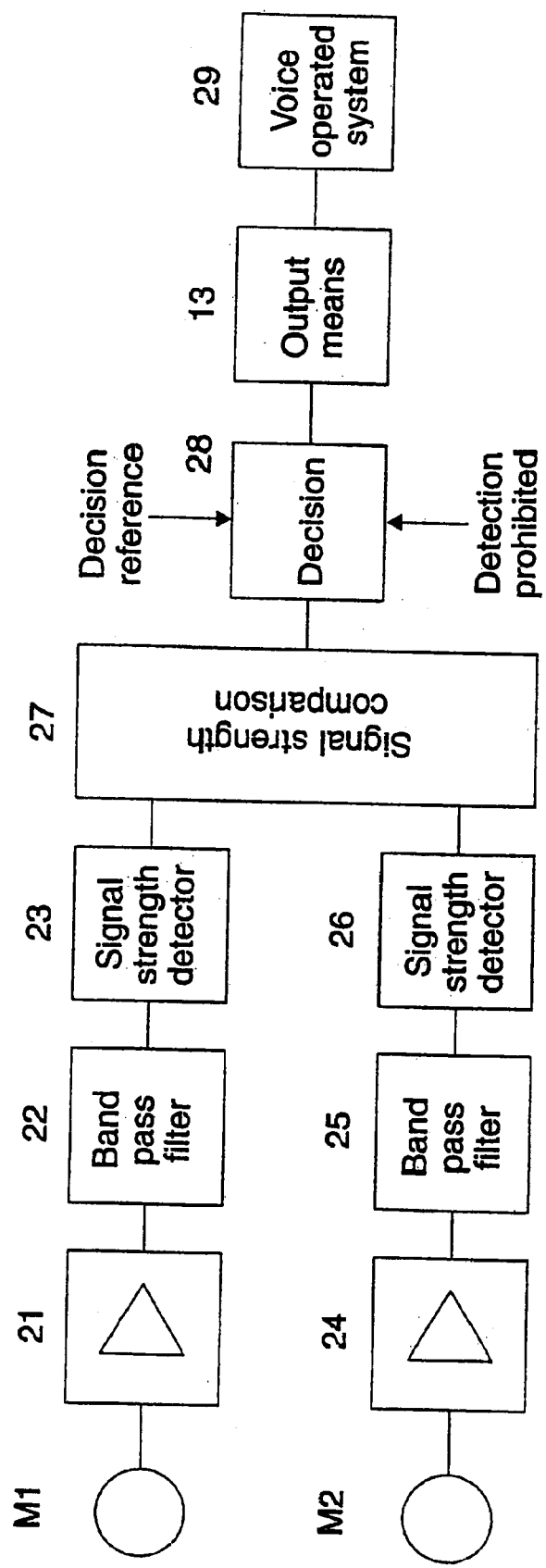
FIG. 3 is a block diagram illustrating one possible signal processing arrangement according to the invention.

The block diagram in FIG. 3 illustrates one possible signal processing arrangement according to the invention. The signal processing may be all analogue, or the amplified signals from M1 and M2 may be A/D-converted and all filtering and signal processing is performed in the digital domain as illustrated by FIG. 2. The signal from electroacoustic transducer element M1 is amplified in amplifier 21 and filtered in a bandpass filter 22 before it is fed to a signal strength detector. Likewise the signal from electroacoustic transducer element M2 is amplified in amplifier 24 and filtered in bandpass filter 25 before it is fed to a signal strength detector 26. The outputs from the two signal strength detectors 23,26 are compared in the signal strength comparison unit 27 which also provides as an output a difference signal representing the difference in signal strength from the two electroacoustic transducer elements.

This difference signal output is input to the decision block 28. The difference signal has a negative dB value. When the difference signal is less negative than a certain limit a decision is made that the user of the equipment is speaking. When the difference signal is more negative than this limit the user is considered not to be speaking. The difference signal is typically in the range of −20 to −40 dB. Typically a suitable value of the limit will be in the range 2 to 10 dB less negative than a typical value of the difference signal for noise alone, for any single apparatus.

The limit is typically stored in the storage means E8,E9, E10 of the apparatus and may be a predetermined value for any single apparatus. The limit is input as the decision reference to to the decision block 28, as indicated in FIG. 3.

However, the limit may be generated during use of the device to accomodate for slow drift in the performance of the apparatus. An adaptive process may be performed in the processing unit E3 in order to obtain this adapted limit. This limit could also be generated in a calibration procedure being performed at regular intervals.

In a similar manner, the limit may be generated during use of the device to accomodate for individual differences between users of the apparatus.

Figure 4:
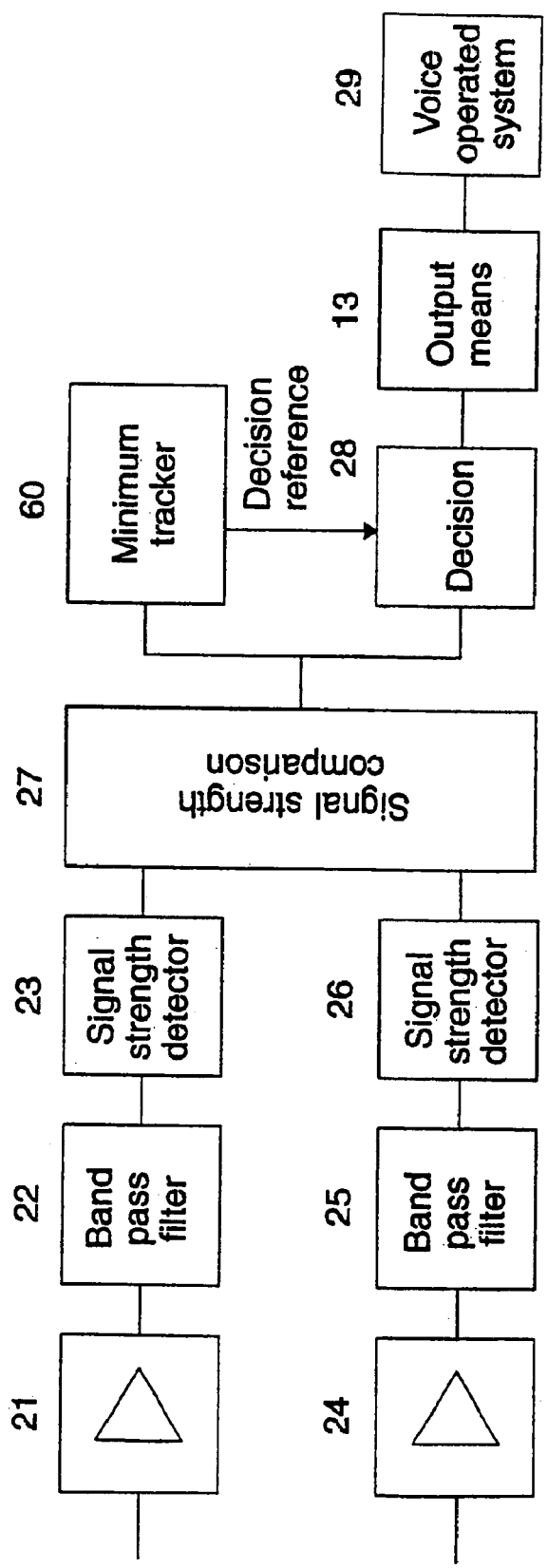
FIG. 4 is a block diagram illustrating one possible signal processing arrangement according to the invention where the decision reference signal input is derived from a minimum tracker.

In an alternative the decision reference signal input may be derived using a minimum tracker 60 as illustrated in FIG. 4. The minimum tracker takes an input signal from the output of the signal strength comparison block 27.

Figure 6:
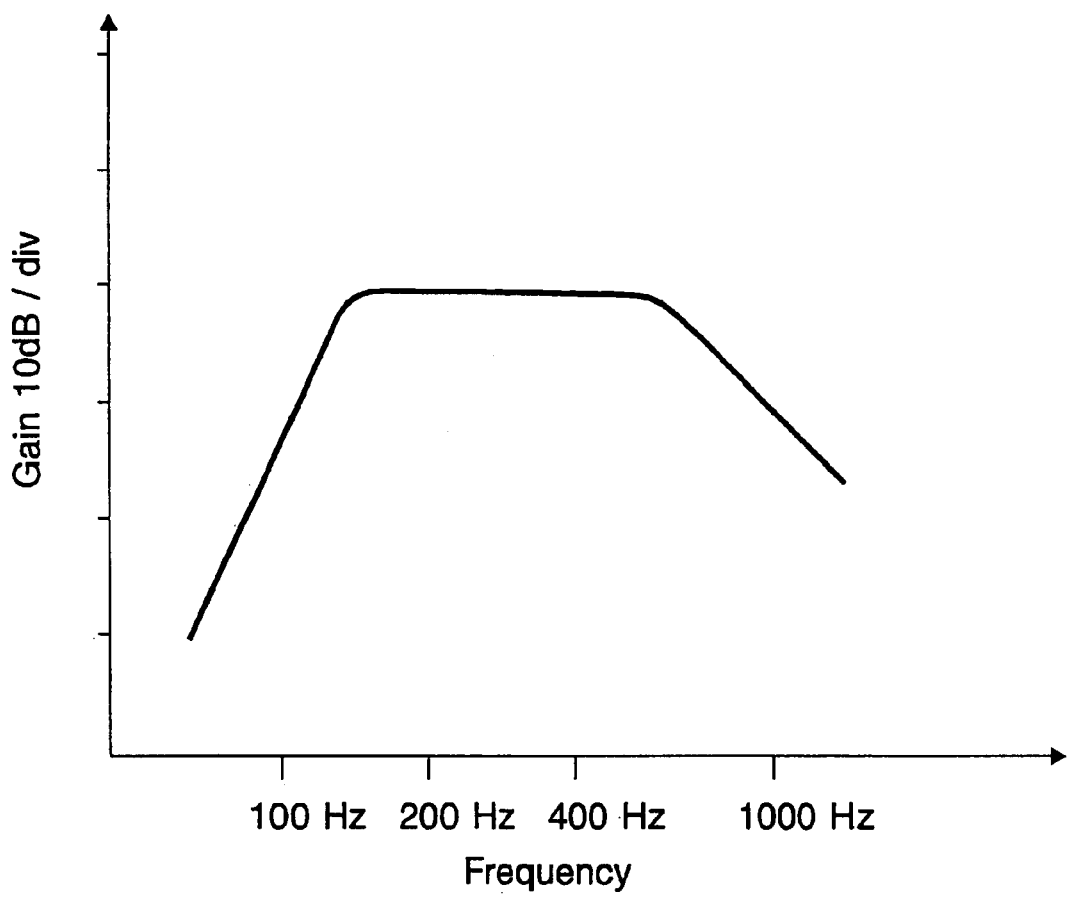
FIG. 6 illustrates a possible frequency response characteristic of the bandpass filters.

A possible characteristic of the bandpass filters is shown in FIG. 6. The diagram shows frequency response with upper and lower cut-off frequencies of 150 Hz and 700 Hz respectively, a highpass slope of +18 dB/octave and a lowpass slope of −6 dB/octave. This frequency characteristic selects a frequency range where the signal strength of the user's voice in the enclosed space in the inner part of the meatus is high. At the same time it suppresses low frequency noise that may be dominating in typical environments (vehicles, factories, etc.)

Figure 7:
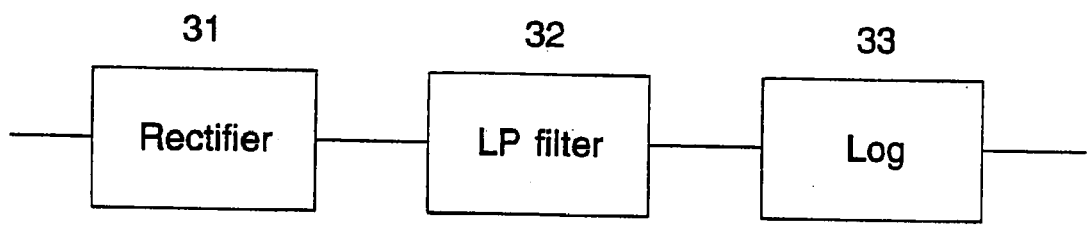
FIG. 7 is a block diagram illustrating a preferred embodiment of the signal detection.

One preferred embodiment of the signal strength detection 23,26 is illustrated in FIG. 7. The bandpass filtered signal from each of the bandpass filters 23,25 is rectified in a rectifier unit 31 and passed on to a lowpass filter 32. A suitable time constant of the lowpass filter is 10 ms. The output signal of the lowpass filter 32 is input to a logarithmic converter 33. The logarithm of the signal from 32 is in a digital version of the invention calculated and output to the comparison block 27. In an analog version the logarithm of the signal from 32 is obtained using an analog logarithmic converter 33. The outputs from the logarithmic converters 33 are fed to the signal strength comparison unit 27.

In the signal strength comparison unit 27 there may be performed a running subtraction of the logarithmic value that is output from the signal strength detector 23 from the logarithmic value that is output from the signal strength detector 26.

If such a signal subtraction is performed when there is no voice signal produced by the user, the result of the subtraction provides a measure of the attenuation of the hearing protecting function of the apparatus (1,2) according to the invention.

If in addition such a running subtraction is performed prior to use of the apparatus, it is possible to obtain a calibration value, being a typical attenuation value of the attenuation of the hearing protecting function of the apparatus (1,2) according to the invention. Such a calibration value would preferably be stored internally in storage means (E8,E9,E10) in the apparatus. In some applications such a calibration could be performed for an intended user of the apparatus.

When such a calibration operation has been performed for an apparatus and for a particular user, a later signal subtraction performed when there is no voice signal produced by the user, the result of the subtraction will be a verification of the continued correct operation of the sound attenuation function of the hearing protecting function of the apparatus (1,2) according to the invention. Correct operation is verified if the result of the subtraction is roughly equal to the value obtained in the calibration operation.

If a calibration operation is performed in a controlled environment with a controllable noise signal generator, it is possible to obtain a calibrated frequency dependent characteristic attenuation of the hearing protecting function of the apparatus (1,2) according to the invention.

Figure 8:
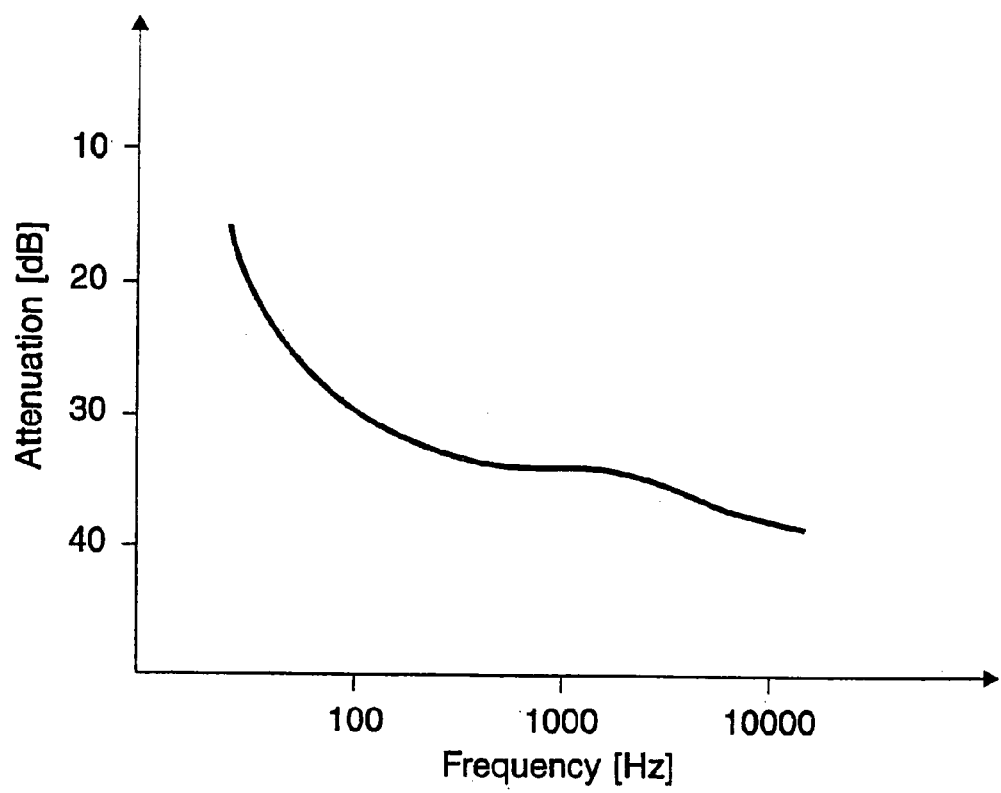
FIG. 8 shows a typical sound attenuation characteristic of a hearing protector with a polymer foam sealing section and active noise control (ANR)

The decision block 28 makes a decision based on the fact that the signal strength difference (calculated in 27) between electroacoustic transducer elements M1 and M2 due to external sounds alone, is independent of the sound character and sound level. It is only dependent on the sound attenuating properties of the hearing protector. These properties are normally independent of sound strength, but dependent on the frequency of the sound. A typical sound attenuation characteristic of a hearing protector with a polymer foam sealing section and active noise control (ANR) is shown in FIG. 8.

When the user of the hearing protector, being in a noisy environments, speaks, the signal from his voice produces a strong signal in electroacoustic transducer element M2 (especially in the frequency range 100 Hz–1 kHz), and the difference, as measured by block 27 in FIG. 3, is diminished. When the frequency dependent attenuation of the hearing protector is known, this gives a very precise functioning of the voice detector compared to a detector that is based on a signal level alone. The detector may act on a limit that is just a few dB less than the attenuation of the hearing protector, without risking false detection due to external noise.

The attenuation characteristic of the hearing protector may be known a priori, or it may be estimated prior to normal use or during use as explained above. A running estimate of the attenuation may be performed by employing a minimum tracker 60 on the signal from the signal strength comparison 27 in FIG. 3.

The result of the signal strength comparison 28 will typically be a constant or slowly varying signal due mainly to the characteristics of the hearing protector 1,2, with fairly short peaks added due to the speech signal when the user speaks. The speech peaks will typically have a duration of 10–30 milliseconds. The interval between the peaks will typically have a duration of 10–500 milliseconds. The decision block 28 may accordingly contain two signal processing steps, the first step 40 being a momentary decision comparing the composite input signal with a reference signal, the second step 41 being a retriggerable timer with a fixed delay of typically 500 milliseconds. The purpose of the retriggerable delay is to bridge the interval between the speech peaks. The output from the retriggerable delay constitutes the final signal signifying the presence of speech.

Figure 9:
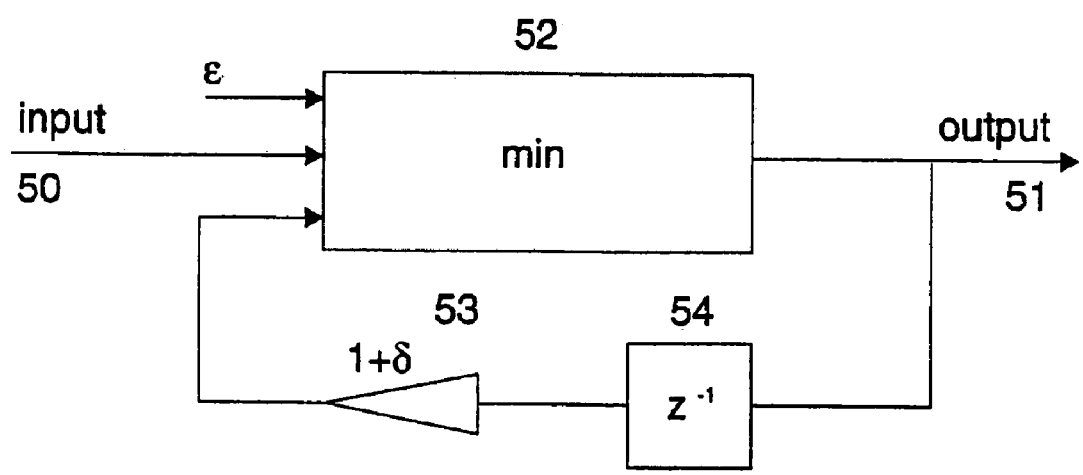
FIG. 9 illustrates the operation of a minimum tracker.

FIG. 9 illustrates the operation of the minimum tracker 60. The minimum tracker 60 outputs the minimum value of the input signal as a function of time. When the input signal is higher than the output signal, the output value increases upwards slowly until it reaches the input value.

The minimum tracker 60 is preferably implemented as a digital filter with a first input 50 to a minimum (min) function block 52 having an output 51. In a feedback loop of the min function block 52 a sample delay block 54 provides a sample delay $1/z$, a multiplication block 53 with a multiplication factor $1+\delta$ provides a multiplication function, the output of which provides a second input to the min function block 52. A third input to the min unction block 52 is provided by a minimum value input 55 set to a minimum value $\epsilon$. The min function block 52 outputs the smallest value of its three inputs, as indicated in FIG. 9.

The minimum value $\epsilon$ provided to the minimum value input 55 is used to avoid the minimum tracker 60 dropping down to a value of zero. If the minimum tracker 60 enters the zero value, it will not recover from this value. The initial value in the delay should thus be $\epsilon$. The range of the positive constants $\delta$ and $\epsilon$ depend on the number format (integer or floating point) and the number of bits in the implementation of the digital filter.

Due to the syllabic nature of speech the output of the minimum tracker 60 represents a measure of the acoustic attenuation of the hearing protector. The limit in the decision block 28 may then be adjusted according to the running estimate of the acoustic attenuation.

Part of the electronics unit 11,E3 and the output means 13 may be contained in a unit being separate from, but connected to said ear terminal 1,2. In some situations it may be required to use signal processing units located in a separate unit, for example due to limited space in the ear terminal element, or due to additional processing functions in auxiliary signal processing units. The output means may in some applications require radio transmitters with output powers undesirable near the users head. In this case part of the output means could be arranged some distance away the head, but connected using a suitable communications interface.

The processing unit E3 may comprise signal analysis means for detecting the presence of speech components, such as words, in the signal from the inner electroacoustic transducer element M2. Upon detecting certain components in the signal particular commands, instructions or code may be fetched from the storage means E8,E9,E10 for transmission to the voice operated system using the output means 13. The signal analysis means may also comprise means for determining the duration, frequency content, and amplitude of the signal from the inner electroacoustic transducer element M2. In particular, the signal analysis means comprises means for separating the voice signal from the total signal detected by the inner electroacoustic transducer element. The signal analysis is typically realised as software modules performing a combination of signal processing functions, such as digitial filtering.

What is claimed is:

1. Voice detection and discrimination apparatus for controlling a voice operated system comprising a protective ear terminal element (1,2) for protecting the ear by providing acoustic attenuation,
   an inner electroacoustic transducer element (M2) on an inner side of the ear terminal element (1,2) for detecting a first acoustic field and providing a first electronic signal representing said first acoustic field,
   an outer electroacoustic transducer element (M1) on an outer side of the ear terminal element (1,2) for detecting a second acoustic field and providing a second electronic signal representing said second acoustic field,
   an electronics unit (11,E3) connected with said electroacoustic transducer elements (M1,M2) and comprising first comparison means (27) for comparison of said first and second electronic signals to obtain the difference between said two electronic signals, and second comparison means (28) for comparing said difference with given criteria, and
   output means (13,E12) connected to said electronics unit for providing an output signal depending on said second comparison, said output signal is an input signal to the voice operated system (29),
   wherein the criteria comprises a predetermined difference in acoustic signal strength as detected by the two electroacoustic transducer elements (M1,M2) in a noisy environment.

2. Apparatus according to claim 1 wherein the output signal comprises instructions, commands, code for said voice operated system, such as a communication system.

3. Apparatus according to claim 1 wherein the criteria are predetermined and stored in storage means (E8,E9,E10) in the apparatus.

4. Apparatus according to claim 1 comprising processing means (E3) for adapting the criteria during use of the apparatus.

5. Apparatus according to claim 1 wherein the predetermined difference in acoustic signal strength as detected by the two electroacoustic transducer elements (M1,M2) in a noisy environment is in the range −20 to −40 dB, and a predetermined allowable decrease of the said difference in acoustic signal strength is in the range of 2 to 10 dB.

6. Apparatus according to claim 1 comprising a first electronic filter (22) for filtering the electronic signal from the inner electroacoustic transducer element (M2).

7. Apparatus according to claim 1 comprising a second electronic filter (25) for filtering the electronic signal from the outer electroacoustic transducer element (M1).

8. Apparatus according to claim 6 comprising electronic bandpass filters (22,25), typically with a passband in the range 150–700 Hz.

9. Apparatus according to claim 8 comprising a signal strength detector (23,26) connected with said bandpass filters (22,25) for providing inputs for a signal strength comparison block (27).

10. Apparatus according to claim 9 comprising a decision block (28) connected with said signal strength comparison block (27) for providing said output signal to said voice operated system (29).

11. Apparatus according to claim 1
    wherein at least a part of the electronics unit (11,E3) and the output means (13) is contained in a unit being separate from, but connected to said ear terminal (1,2).

12. Apparatus according to claim 1
    wherein said ear terminal element (1,2) comprises an ear plug section (1) and a sealing section (2) forming a hearing protector (1,2) for placement in an ear and for protection of the hearing function.

13. Voice detection and discrimination apparatus for controlling a voice operated system comprising
    a protective ear terminal element (1,2) for protecting the ear by providing acoustic attenuation,
    an inner electroacoustic transducer element (M2) on an inner side of the ear terminal element (1,2) for detecting a first acoustic field and providing a first electronic signal representing said first acoustic field,
    an outer electroacoustic transducer element (M1) on an outer side of the ear terminal element (1,2) for detecting a second acoustic field and providing a second electronic signal representing said second acoustic field,
    an electronics unit (11,E3) connected with said electroacoustic transducer elements (M1,M2) and comprising first comparison means (27) for comparison of said first and second electronic signals to obtain the difference between said two electronic signals, and second comparison means (28) for comparing said difference with given criteria, and output means (13,E12) connected to said electronics unit for providing an output signal depending on said second comparison, said output signal is an input signal to the voice operated system (29)

wherein the signal strength comparison means (27) comprises means for estimating the acoustic attenuation of the ear terminal element (1,2) for establishing said predetermined difference.

14. Apparatus according to claim 13 comprising a minimum tracker (60) connected with the detectors (23,26) for obtaining running estimates of the said acoustic attenuation.

15. Apparatus according to claim 1, wherein the electronics unit (11,E3) comprises signal analysis means (E3) for extracting a voice signal from the inner electroacoustic transducer element (M2), for transmission to the voice operated system.

16. Apparatus according to claim 15, comprising signal analysis means (E3) for detecting the presence of particular speech components, such as words, in the signal from the inner electroacoustic transducer element (M2), for forming commands, instructions or code for the voice operated system (29).

17. Apparatus according to claim 1 wherein the electroacoustic transducer element(s) (M1, M2) is(are) microphones.

18. Method of detecting a voice and for controlling a voice operated system, employing an ear terminal element (1,2) for protecting the ear by providing acoustic attenuation comprising the following steps;

detecting (M2) the acoustic signal strength on the inner side of said ear terminal element, detecting (M1) the acoustic signal strength on the outer side of said ear terminal element, obtaining (23,26,27) a difference value representing the difference in the acoustic signal strength between the inner and outer side of said ear terminal element, deciding (28) if a voice is present using said value representing said difference and given criteria (28), providing an output signal depending on said decision using output means (13,E12), the output signal being an input to the voice operated system (29), and determining if said difference in the acoustic signal strength (27) between the inner and outer side of said ear terminal element (1,2) has decreased more than a given amount.

19. Method according to claim 18 comprising providing an output signal (13) in the form of a control signal, commands, instructions, code for said voice operated system (29), such as a communication system.

20. Method according to claim 18 comprising writing and reading predetermined criteria to and from storage means (E8,E9,E10) in the ear terminal element (1,2).

21. Method according to claim 18 comprising determining if said difference in the acoustic signal strength (27) between the inner and outer side of said ear terminal element (1,2) has decreased more than a given amount, typically 2–10 dB, from a predetermined amount, typically −20 to −40 dB.

22. Method according to claim 18 comprising filtering (22,25) the signals from the two electroacoustic transducer elements (M2,M1) using bandpass filters (22,25).

23. Method according to claim 18 comprising;

analysing (E3) the voice signal for determining its characteristic, such as duration, frequency, and amplitude, providing said output signal (13) depending on the said determined voice characteristics.

24. Method according to claim 23 comprising;

obtaining a value representing the running average of the difference in the acoustic signal level between the inner and outer side of the ear terminal element (1,2).

25. Method according to claim 18 comprising adjusting the said criteria according to the running average of the said difference.

26. Method according to claim 18 comprising extracting information from the acoustic signals being detected by the electroacoustic transducer elements (M1,M2).

27. Method according to claim 26 comprising analysing the signal from the electroacoustic transducer elements (M1,M2) for the presence of particular speech components, such as words.

28. Method according to claim 18 comprising prior to normal use, performing a calibration operation where an estimate of the attenuation of the hearing protector is obtained by determining the difference in the sound levels as detected by the two electroacoustic transducer elements in a period where no voice but only noise is present.

29. Method according to claim 18 comprising during normal operation, performing a verification operation where an estimate of the attenuation of the hearing protector is obtained by determining the difference in the sound levels as detected by the two electroacoustic transducer elements in a period where no voice but only noise is present, and the obtained attenuation is compared with a predetermined stored attenuation value.

30. Voice detection and discrimination apparatus for controlling a voice operated system comprising a protective ear terminal element (1,2) for protecting the ear by providing acoustic attenuation, an inner electroacoustic transducer element (M2) on an inner side of the ear terminal element (1,2) for detecting a first acoustic field and providing a first electronic signal representing said first acoustic field, an outer electroacoustic transducer element (M1) on an outer side of the ear terminal element (1,2) for detecting a second acoustic field and providing a second electronic signal representing said second acoustic field, an electronics unit (11,E3) connected with said electroacoustic transducer elements (M1,M2) and comprising first comparison means (27) for comparison of said first and second electronic signals to obtain the difference between said two electronic signals, and second comparison means (28) for comparing said difference with given criteria, output means (13,E12) connected to said electronics unit for providing an output signal depending on said second comparison, said output signal is an input signal to the voice operated system (29), and a decision block with a detection prohibition function in order to enable a blocking function in the ear terminal when an incoming communication signal is introduced in the ear terminal.

31. Apparatus according to claim 13 wherein the output signal comprises instructions, commands, code for said voice operated system, such as a communication system.

32. Apparatus according to claim 13 wherein the criteria are predetermined and stored in storage means (E8,E9,E10) in the apparatus.

33. Apparatus according to claim 13 comprising processing means (E3) for adapting the criteria during use of the apparatus.

34. Apparatus according to claim 13 wherein the predetermined difference in acoustic signal strength as detected by the two electroacoustic transducer elements (M1,M2) in a noisy environment is in the range −20 to −40 dB, and a predetermined allowable decrease of the said difference in acoustic signal strength is in the range of 2 to 10 dB.

35. Apparatus according to claim 13 comprising a first electronic filter (22) for filtering the electronic signal from the inner electroacoustic transducer element (M2).

36. Apparatus according to claim 13 comprising a second electronic filter (25) for filtering the electronic signal from the outer electroacoustic transducer element (M1).

37. Apparatus according to claim 35 comprising electronic bandpass filters (22,25), typically with a passband in the range 150–700 Hz.

38. Apparatus according to claim 37 comprising a signal strength detector (23,26) connected with said bandpass filters (22,25) for providing inputs for a signal strength comparison block (27).

39. Apparatus according to claim 38 comprising a decision block (28) connected with said signal strength comparison block (27) for providing said output signal to said voice operated system (29).

40. Apparatus according to claim 13
wherein at least a part of the electronics unit (11,E3) and the output means (13) is contained in a unit being separate from, but connected to said ear terminal (1,2).

41. Apparatus according to claim 13
wherein said ear terminal element (1,2) comprises an ear plug section (1) and a sealing section (2) forming a hearing protector (1,2) for placement in an ear and for protection of the hearing function.

42. Apparatus according to claim 13,
wherein the electronics unit (11,E3) comprises signal analysis means (E3) for extracting a voice signal from the inner electroacoustic transducer element (M2), for transmission to the voice operated system.

43. Apparatus according to claim 42,
comprising signal analysis means (E3) for detecting the presence of particular speech components, such as words, in the signal from the inner electroacoustic transducer element (M2), for forming commands, instructions or code for the voice operated system (29).

44. Apparatus according to claim 13
wherein the electroacoustic transducer element(s) (M1, M2) is(are) microphones.

45. Method of detecting a voice and for controlling a voice operated system, employing an ear terminal element (1,2) for protecting the ear by providing acoustic attenuation comprising the following steps;
detecting (M2) the acoustic signal strength on the inner side of said ear terminal element,
detecting (M1) the acoustic signal strength on the outer side of said ear terminal element,
obtaining (23,26,27) a difference value representing the difference in the acoustic signal strength between the inner and outer side of said ear terminal element,
deciding (28) if a voice is present using said value representing said difference and given criteria (28),
providing an output signal depending on said decision using output means (13,E12), the output signal being an input to the voice operated system (29), and
adjusting the said criteria according to the running average of the said difference.

46. Method according to claim 45 comprising
providing an output signal (13) in the form of a control signal, commands, instructions, code for said voice operated system (29), such as a communication system.

47. Method according to claim 45 comprising
writing and reading predetermined criteria to and from storage means (E8,E9,E10) in the ear terminal element (1,2).

48. Method according to claim 45 comprising
determining if said difference in the acoustic signal strength (27) between the inner and outer side of said ear terminal element (1,2) has decreased more than a given amount, typically 2–10 dB, from a predetermined amount, typically −20 to −40 dB.

49. Method according to claim 45 comprising
filtering (22,25) the signals from the two electroacoustic transducer elements (M2,M1) using bandpass filters (22,25).

50. Method according to claim 45 comprising;
analysing (E3) the voice signal for determining its characteristic, such as duration, frequency, and amplitude,
providing said output signal (13) depending on the said determined voice characteristics.

51. Method according to claim 50 comprising;
obtaining a value representing the running average of the difference in the acoustic signal level between the inner and outer side of the ear terminal element (1,2).

52. Method according to claim 45 comprising
extracting information from the acoustic signals being detected by the electroacoustic transducer elements (M1,M2).

53. Method according to claim 52 comprising
analysing the signal from the electroacoustic transducer elements (M1,M2) for the presence of particular speech components, such as words.

54. Method according to claim 45 comprising
prior to normal use, performing a calibration operation where an estimate of the attenuation of the hearing protector is obtained by determining the difference in the sound levels as detected by the two electroacoustic transducer elements in a period where no voice but only noise is present.

55. Method according to claim 45 comprising
during normal operation, performing a verification operation where an estimate of the attenuation of the hearing protector is obtained by determining the difference in the sound levels as detected by the two electroacoustic transducer elements in a period where no voice but only noise is present, and the obtained attenuation is compared with a predetermined stored attenuation value.

56. Method of detecting a voice and for controlling a voice operated system, employing an ear terminal element (1,2) for protecting the ear by providing acoustic attenuation comprising the following steps;
detecting (M2) the acoustic signal strength on the inner side of said ear terminal element,
detecting (M1) the acoustic signal strength on the outer side of said ear terminal element,
obtaining (23,26,27) a difference value representing the difference in the acoustic signal strength between the inner and outer side of said ear terminal element, deciding (28) if a voice is present using said value representing said difference and given criteria (28), providing an output signal depending on said decision using output means (13,E12), the output signal being an input to the voice operated system (29), and during normal operation, performing a verification operation where an estimate of the attenuation of the hearing protector is obtained by determining the difference in the sound levels as detected by the two electroacoustic transducer elements in a period where no voice but only noise is present, and the obtained attenuation is compared with a predetermined stored attenuation value.

57. Method according to claim 56 comprising providing an output signal (13) in the form of a control signal, commands, instructions, code for said voice operated system (29), such as a communication system.

58. Method according to claim 56 comprising writing and reading predetermined criteria to and from storage means (E8,E9,E10) in the ear terminal element (1,2).

59. Method according to claim 56 comprising determining if said difference in the acoustic signal strength (27) between the inner and outer side of said ear terminal element (1,2) has decreased more than a given amount, typically 2–10 dB, from a predetermined amount, typically −20 to −40 dB.

60. Method according to claim 56 comprising;

filtering (22,25) the signals from the two electroacoustic transducer elements (M2,M1) using bandpass filters (22,25).

61. Method according to claim 56 comprising;

analysing (E3) the voice signal for determining its characteristic, such as duration, frequency, and amplitude, providing said output signal (13) depending on the said determined voice characteristics.

62. Method according to claim 61 comprising;

obtaining a value representing the running average of the difference in the acoustic signal level between the inner and outer side of the ear terminal element (1,2).

63. Method according to claim 56 comprising adjusting the said criteria according to the running average of the said difference.

64. Method according to claim 56 comprising extracting information from the acoustic signals being detected by the electroacoustic transducer elements (M1,M2).

65. Method according to claim 64 comprising analysing the signal from the electroacoustic transducer elements (M1,M2) for the presence of particular speech components, such as words.

66. Method according to claim 56 comprising prior to normal use, performing a calibration operation where an estimate of the attenuation of the hearing protector is obtained by determining the difference in the sound levels as detected by the two electroacoustic transducer elements in a period where no voice but only noise is present.

* * * * *